(12) United States Patent
Quirch et al.

(10) Patent No.: US 7,272,975 B2
(45) Date of Patent: Sep. 25, 2007

(54) ULTRASONIC BEAM SHAPING DEVICE

(75) Inventors: Jo-Ana Quirch, Tarrytown, NY (US); Nicolae Dumitrescu, Stamford, CT (US); Luigi Cantatore, White Plains, NY (US)

(73) Assignee: Bayer Healthcare LLC, Tarrytown, NY (US)

( * ) Notice: Subject to any disclaimer, the term of this patent is extended or adjusted under 35 U.S.C. 154(b) by 243 days.

(21) Appl. No.: 11/056,130

(22) Filed: Feb. 11, 2005

(65) Prior Publication Data

US 2006/0236766 A1 Oct. 26, 2006

(51) Int. Cl.
*G01F 23/296* (2006.01)
(52) U.S. Cl. ..................... 73/642; 73/290 V
(58) Field of Classification Search .............. 73/290 V, 73/642, 644
See application file for complete search history.

(56) References Cited

U.S. PATENT DOCUMENTS 3,472,065 A * 10/1969 Maxwell ..................... 73/642
5,001,932 A * 3/1991 Light et al. ..................... 73/644
6,095,979 A * 8/2000 Ohtomo ..................... 600/449
6,227,053 B1 5/2001 Purpura et al.
6,598,474 B2 7/2003 Purpura et al.

OTHER PUBLICATIONS

"PCT International Search Report", International Application No.: PCT/US06/04758, International Filing Date: Feb. 10, 2006, Earliest Priority Date: Feb. 11, 2005, Applicant: Bayer HealthCare LLC.

\* cited by examiner

*Primary Examiner*—John E. Chapman
(74) *Attorney, Agent, or Firm*—Andrew L. Klawitter; Chien Yuan; Rodman & Rodman

(57) ABSTRACT

An ultrasonic beam shaping device includes a plate-like beam shaping element formed of opaque material. The beam shaping element has first and second conical surfaces, with a common axis, formed as opposite surface portions of the beam shaping element. A cylindrical aperture is formed in the beam shaping element along the common axis of the first and second conical surfaces such that the cylindrical aperture is also co-axial with the conical surfaces and passes through the conical surfaces. The beam shaping element thus has a circular open end at each conical surface.

13 Claims, 8 Drawing Sheets

Ultrasonic Transducer
Emitted Energy
Cone Width

Target

Ultrasonic Transducer
Emitted Energy
Cone Width
With Conical Element

Ultrasonic Transducer
Reflected Energy

Target

Ultrasonic Transducer
Reflected Energy
With Conical Element

ULTRASONIC BEAM SHAPING DEVICE

BACKGROUND OF THE INVENTION

This invention relates to ultrasonic liquid level sensing systems, and more particularly to an ultrasonic beam shaping device that tailors the shape of a transducer beam emitted toward a target, tailors the shape of the return beam received by the transducer after being reflected from the target, and diverts from the transducer and target, extraneous unusable portions of the emitted and reflected transducer beams.

In one known automated sample analysis system which employs sample tubes in tube racks, a plurality of containers or sample tubes, capped or uncapped, and of different size and shape may be held in the sample tube racks. The sample tube racks are automatically transported from one location to another within the sample analysis system for selected automated processing operations.

As disclosed in U.S. Pat. No. 6,227,053 to Purpura et al, automated processing of sample tubes in sample tube racks is facilitated by developing an ultrasonic profile of the sample tubes. An ultrasonic liquid level sensor provides data relating to the type of sample tubes in the sample tube rack, indicating whether the sample tubes are capped or uncapped, and also provides data relating to the liquid level in the sample tubes, if the tubes are uncapped.

The ultrasonic sensor includes a transducer that is operable as a transmitter and a receiver. For example, the transducer can emit an ultrasonic burst that is transmitted in air toward a target. When the ultrasonic burst strikes the target, a portion of the ultrasonic wave is reflected back toward the transducer. The reflected wave is characterized as an echo or beam and a reflected wave can produce one or more echoes.

When the transducer detects the reflected waves or echoes it functions as a receiver. The time lapse between the emission of an ultrasonic burst and the detection of the echo provides data for determining the type of container that is targeted by the transducer.

It is known that an ultrasonic burst diverges and propagates along its travel path as a cone shaped wave. The diversionary spread of the cone shaped wave can extend relatively far beyond the peripheral extremities of a particular target container, such that the echoes may produce relatively indistinct imaging of the container profile as shown, for example, in FIG. 10. An ultrasonic beam of narrower cone width produces echoes that provide higher resolution profiling and a more distinct imaging of the container profile as shown, for example, in FIGS. 11 and 12.

In order to produce an ultrasonic beam transmission having a narrow cone-width it is usually necessary to provide an ultrasonic crystal having a geometry and size that corresponds to a narrow-cone beam emission. However, ultrasonic beam transmissions that have a narrow-cone beam emission pattern generally have reduced emitted energy and reduced sensing range, which can adversely affect the resolution capability of an ultrasonic sensing system.

It is thus desirable to provide a system and method for high resolution profiling of targets, with an ultrasonic transducer that normally produces a beam of relatively wide cone-width. It is also desirable to provide a system and method for reshaping an ultrasonic beam emitted by an ultrasonic transducer without reducing the emitted energy of the ultrasonic beam and without causing extraneous, unusable portions of the emitted and reflected beams to interfere with a liquid level sensing system

OBJECTS OF THE INVENTION

Among the several objects of the invention may be noted the provision of a novel beam shaping device for an ultrasonic liquid level sensing system, a novel beam shaping element for an ultrasonic liquid level sensing system that reduces the cone width of the beam without reducing the emitted energy of the ultrasonic beam, a novel beam shaping device for an ultrasonic liquid level sensing system that utilizes a central section of an emitted beam while deflecting outer extraneous sections of the emitted energy beam from the intended target and from the ultrasonic transducer, a novel beam shaping device for an ultrasonic liquid level sensing system that utilizes a central section of a reflected wave while deflecting outer extraneous sections of the reflected wave from the ultrasonic transducer, and a novel method of reducing ultrasonic reflections and echoes from a target surface during ultrasonic liquid level sensing. Other objects and features will be in part apparent, and in part pointed out hereinafter.

DETAILED DESCRIPTION OF THE INVENTION

Figure 1:
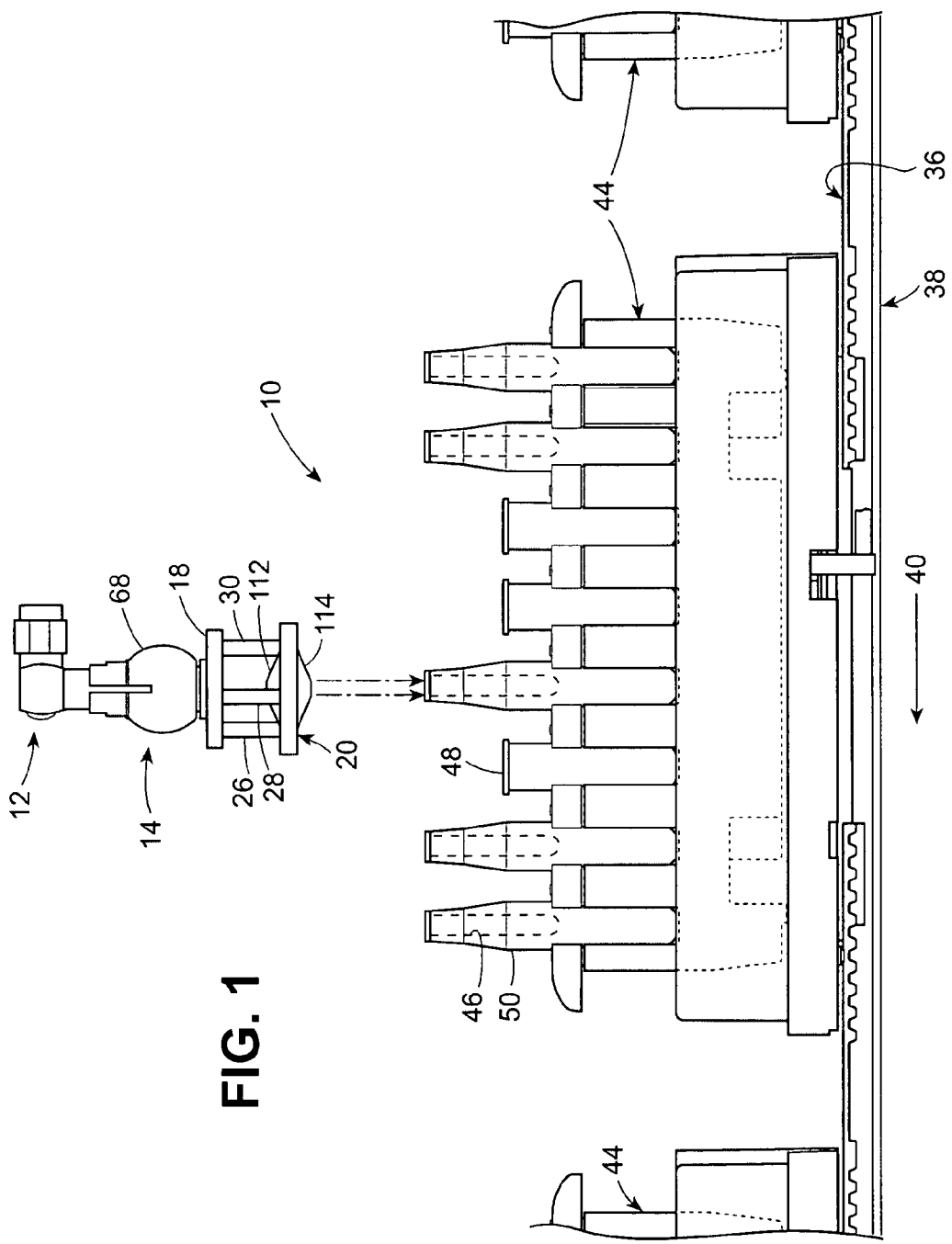
FIG. 1 is a simplified schematic diagram of an ultrasonic liquid level sensing system incorporating one embodiment of the present invention, positioned over a moving sequence of sample tube racks.

Referring to the drawings, FIG. 1 shows in simplified schematic form a portion of an ultrasonic liquid level sensing system 10 including a transducer module 12 supported in a mounting hub or mounting member 14 that holds a mounting plate 18. As used herein the terms "transducer" and "transducer module" will be used interchangeably except where otherwise indicated. A beam shaping device, incorporating one embodiment of the invention, includes a beam shaping element 20 spaced below the mounting plate 18 by a set of identical spacer legs 26, 28 and 30.

The beam shaping element 20 can be formed of any suitable opaque material such as black anodized aluminum. Aluminum can also be used in the formation of the mounting member 14, the mounting plate 18 and the spacer legs 26, 28 and 30.

Figure 2:
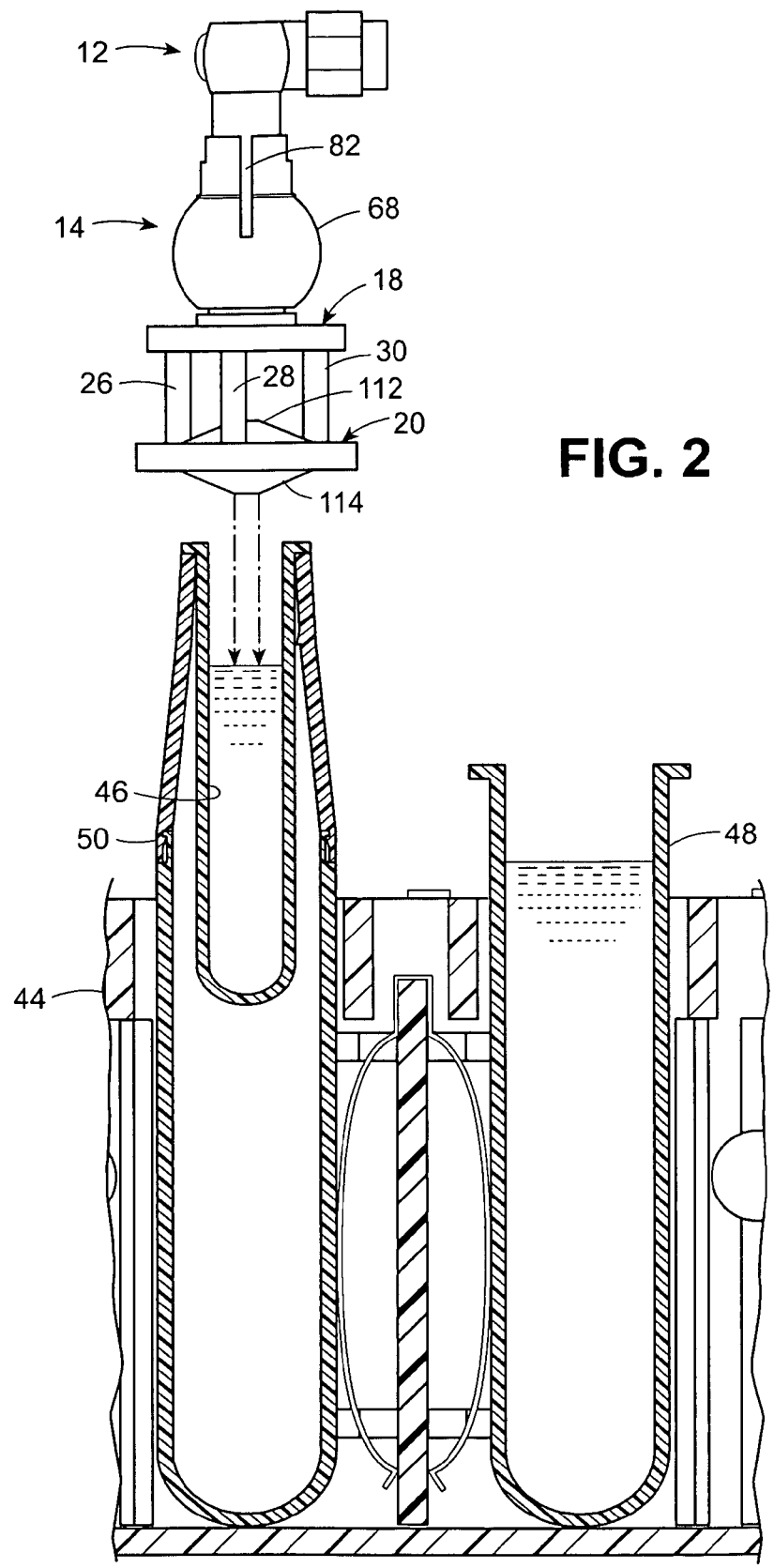
FIG. 2 is an enlarged fragmentary view thereof, partly shown in section.

The ultrasonic liquid level sensing system 10 is held in a fixed position over a conveyor system 36 by any suitable known support structure (not shown). The conveyor system 36 includes a conveyor belt 38 that moves in a horizontal direction such as the direction 40 (FIG. 1) to transport sample tube racks 44, containing sample tubes, which can be of different size, such as 46 and 48 (FIG. 2), to a processing station (not shown). The sample tubes 46 and 48 may be capped or uncapped. Smaller size sample tubes such as the tube 46 can be supported in an adapter 50 that is also held in the sample tube rack 44.

Preferably the beam shaping element 20 should be as close as possible to an intended target, such as the tubes 46 and 48 (FIG. 2), without interfering with the intended target. The closer the transducer 12 is to an intended target, the higher the resolution of the profile image of the target.

Since the tubes 46 and 48 have different elevations, the system 10 is supported relative to the tubes 46 and 48 to enable the beam shaping element 20 to be positioned closely above the highest elevation tube 46. For example, a close yet feasible distance between the beam shaping element 20 and the top of the tube 46 (FIG. 2) can be approximately one-eighth of an inch.

Figure 3:
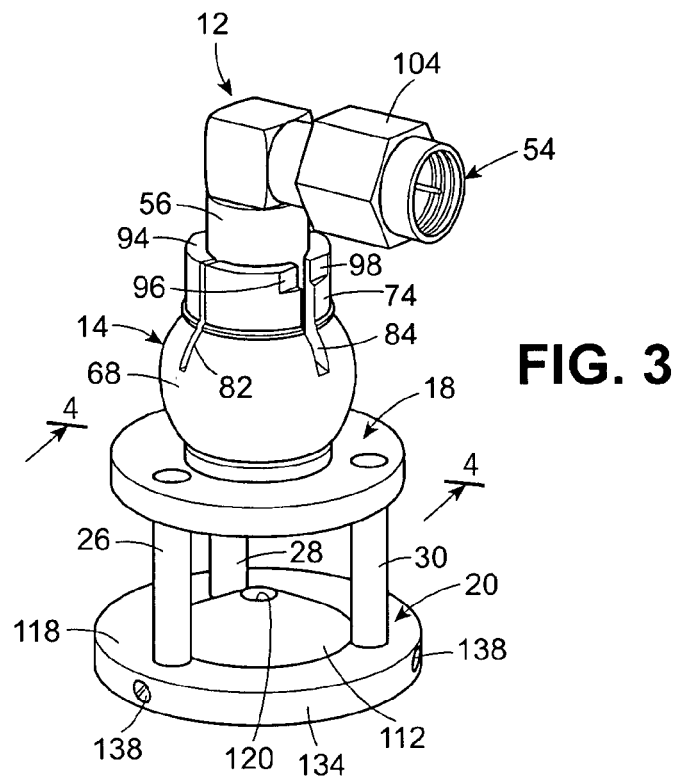
FIG. 3 is a perspective view thereof, including a mounting system for an ultrasonic transducer and the beam shaping device of the present invention.
Figure 4:
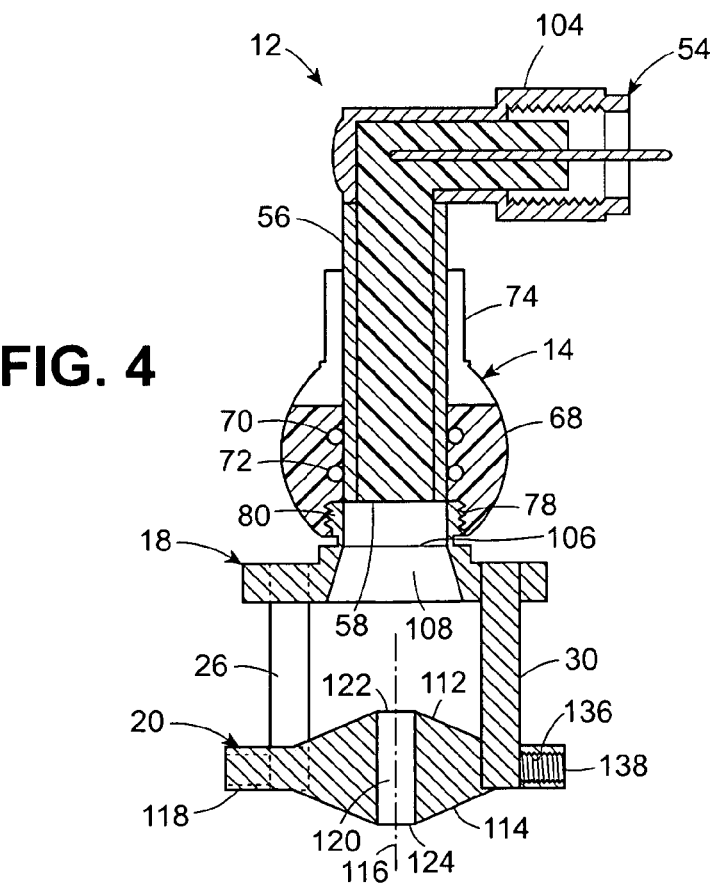
FIG. 4 is a sectional view taken on the line 4-4 of FIG. 3.
Figure 5:
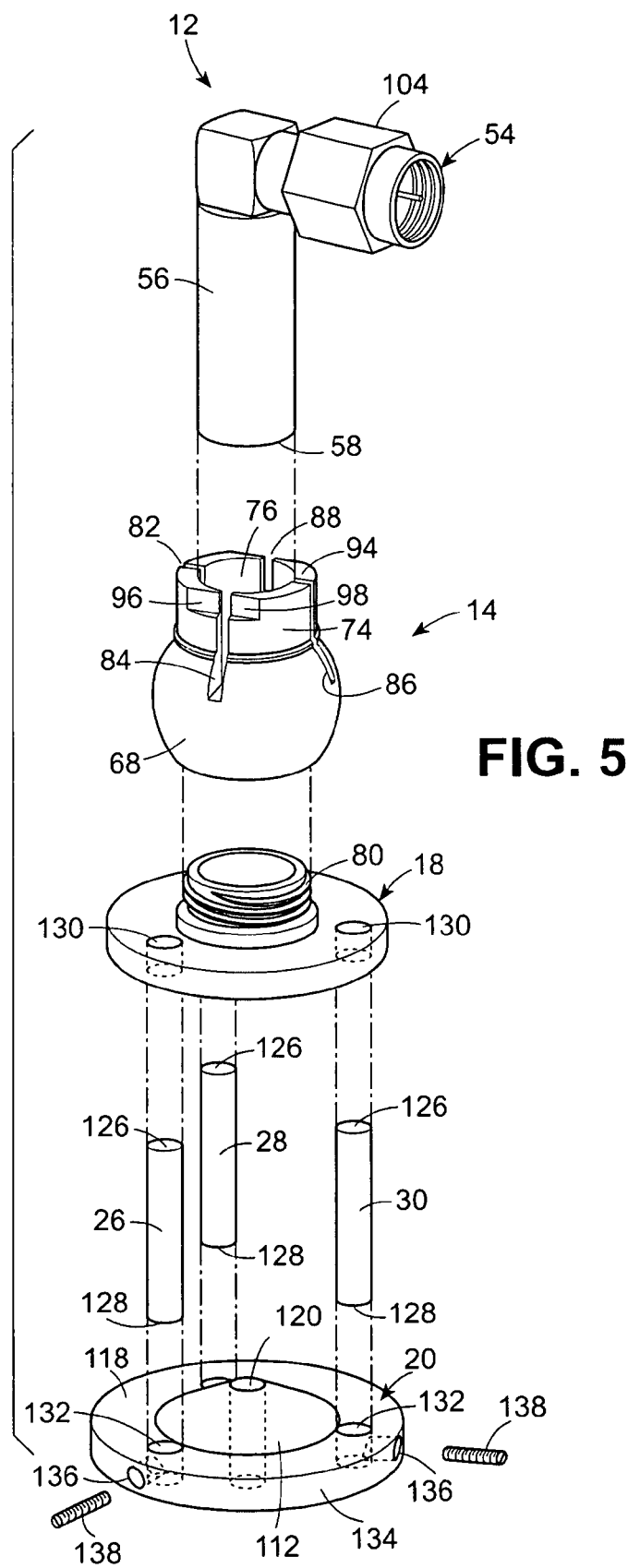
FIG. 5 is an exploded view thereof.

Referring to FIGS. 3-5 the transducer module 12 is of any suitable known construction such as part number 123-10005 made by Cosense, Inc. of Hauppauge, N.Y. The transducer module 12 includes a coaxial connector 54 that connects to any suitable known signal processing and data acquisition electronics system (not shown) for operating the transducer 12. The transducer module 12 also includes a cylindrical leg portion 56 (FIG. 5) having a beam emission end 58 through which a transducer beam is emitted.

As shown most clearly in FIGS. 4 and 5, the mounting hub 14 has a spherical main body portion 68, an annular neck portion 74, and a receiving bore 76 (FIG. 5) extending through the annular neck 74 and the spherical body 68 for receiving the cylindrical leg 56 of the transducer module 12. The receiving bore 76 can have an inner diameter of approximately 8.2 mm for example.

A threaded counterbore 78 (FIG. 4) is formed at a lower end of the receiving bore 76 in the spherical main body portion 68 (FIG. 5) for engagement with a threaded collar 80 projecting from an upper side of the mounting plate 18. The threaded collar can have an inner diameter of approximately 8.5 mm.

The receiving bore 76 (FIG. 4) at the spherical main body portion 68 includes a pair of "O" rings 70 and 72 seated in annular grooves formed in the surface of the bore 76. The bore 76 and the inner diameter of the "O" rings 70 and 72 are sized to permit manually adjustable slidable movement of the transducer leg 56 within the receiving bore 76.

To further facilitate movement of the transducer leg 56 within the receiving bore 76 the annular neck portion 74 of the mounting hub 14 is formed with vertical slots 82, 84, 86 and 88 (FIG. 5) that extend from an upper end 94 of the cylindrical neck portion 74 part-way into the spherical main body 68. Once the transducer 12 is placed in a selected position within the mounting hub 14, any suitable known clamp (not shown) can be placed around the cylindrical neck portion 74 to lock the neck portion 74 against the transducer 12, and thereby secure the transducer 12 in a fixed position relative to the mounting hub 14.

Flat portions 96 and 98 (FIGS. 3 and 5) are formed on the cylindrical neck portion 74 alongside the vertical slots 84 and 88 at the neck end 94 to provide any needed clearance for a co-axial cable tightening nut 104 (FIG. 3) of the co-axial connector 54, when the transducer leg 56 is recessed in the mounting hub 14. During recession of the transducer leg 56 in the mounting hub 14 the beam emission end 58 (FIG. 4) is preferably located proximate a top portion 106 (FIG. 4) of a diverging beam emission opening 108 in the mounting plate 18. The angle between opposite sides of the beam emission opening 108 can be approximately 30° for example and have an axial length of approximately 4.7 mm.

The beam shaping element 20 (FIG. 4) is in the form of a plate that includes symmetrical upper and lower co-axial right conical surfaces 112 and 114 having a common axis 116 and a cone angle that is based on the beam angle of the transducer 12. For example, it has been found that a cone angle of 25° measured between the conical surface 112 or 114 and the horizontal provides satisfactory results with a transducer 12 having a beam angle of approximately 4° measured between opposite sides of the beam.

The beam shaping element 20 is bordered by an annular peripheral rim 118 at the extremity of the conical surfaces 112 and 114. A central cylindrical aperture 120 has a diameter that is dependent on the diameter of the ultrasonic crystal in the transducer 12. For example an aperture 120 of 3 to 7 mm in diameter, suitably corresponds to an ultrasonic crystal diameter of approximately 5 mm, for example. The aperture 120 extends along the axis 116 of the conical surfaces 112 and 114 such that the axis 116 is also the central axis of the cylindrical aperture 120. The axis 116 is also co-axial with the centerline of the ultrasonic transducer 12. The cylindrical aperture 120 includes first and second open ends 122 and 124 (FIG. 4) at the respective first and second conical surfaces 112, 114.

The conical surfaces 112 and 114 can have a diameter up to the peripheral rim 118 of approximately 16 mm for example and the outer diameter of the peripheral rim 118 can be approximately 27 mm, for example. The thickness of the peripheral rim can be approximately 3.5 mm for example.

Referring to FIG. 5, the spacer legs 26, 28 and 30, which can be approximately ¾ of an inch long, for example, have opposite end portions 126 and 128. The end portions 126 are fixed in three equally spaced openings 130 in the mounting plate 18, by bonding or staking for example. The spacer leg end portions 128 are respectively positioned in three equally spaced openings 132 in the annular rim 118 of the beam shaping element 20.

A peripheral edge 134 (FIGS. 3 and 5) of the rim 118 is provided with three threaded openings 136 that are each arranged to intersect with a respective spacer leg opening 132 in the manner shown in FIG. 4. A setscrew 138 is provided in each of the threaded openings 136 to secure the beam shaping element 20 to the respective spacer legs 26, 28 and 30.

A selected distance between the beam shaping element 20 and the mounting plate 18 is obtainable by loosening the setscrews 138, shifting the beam shaping element along the spacer legs 26, 28 and 30 and then tightening the setscrews 138 at a desired spacing between the beam shaping element 20 and the mounting plate 18.

Under this arrangement the means for adjusting the distance between beam shaping element 20 and the transducer module 12 include the mounting plate 18 and the spacer legs 26, 28 and 30. The distance between the top portion 106 of the diverging beam emission opening 108 and the bottom of the peripheral rim 118 can be approximately 22.5 mm for example.

Figure 6:
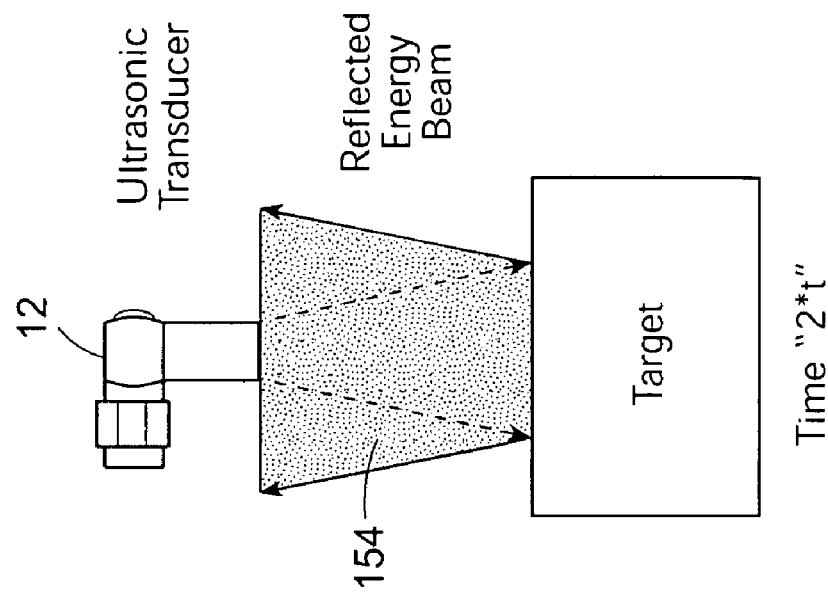
FIGS. 6 and 7 are simplified schematic views of an ultrasonic liquid level sensing system without a beam shaping device.

During ultrasonic liquid level sensing or ultrasonic profiling, the transducer module 12 (FIG. 6) emits an ultrasonic burst of energy 150 aimed at a target 152 moving underneath the transducer 12 in a horizontal direction corresponding to the direction 40 of the conveyor belt 38 (FIG. 1). When the ultrasonic burst 150 reaches the target 152, and depending on the geometry of the target, some of the energy of the ultrasonic burst 150 is reflected back as a reflected beam 154 (FIG. 7) toward the transducer 12 as an echo. The elapsed time between the energy burst 150 and the sensed echo from the reflected beam 154 is directly proportional to the distance "$d_T$" (FIG. 6) of the target 152 from the transducer 12.

Figure 8:
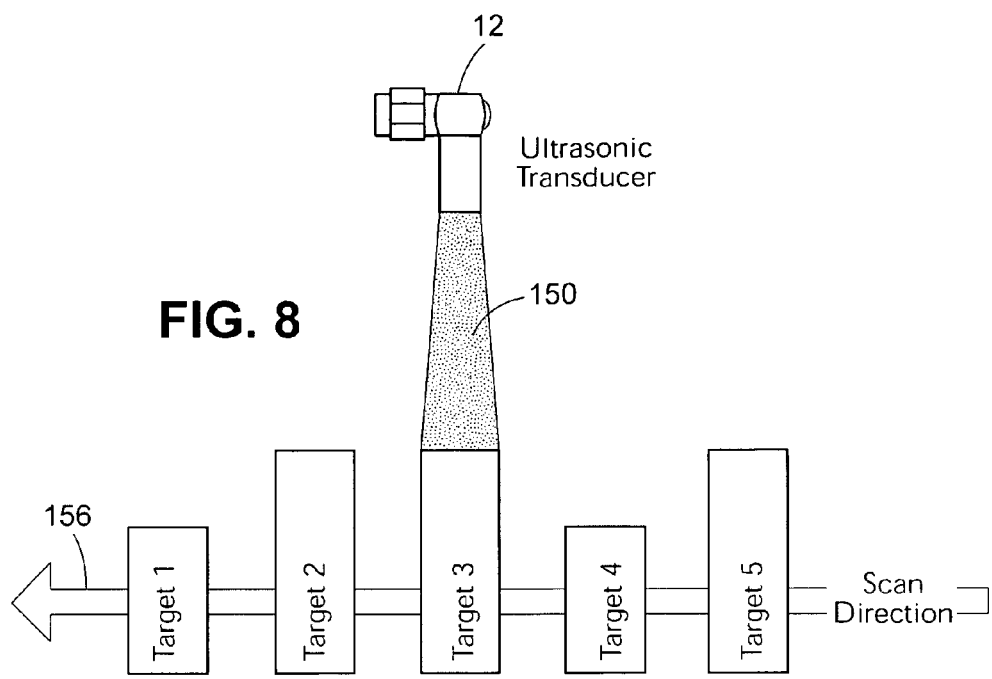
FIG. 8 is a simplified view of an ultrasonic liquid level sensing system, without a beam shaping device, as used to measure targets of different size.

Referring to FIG. 8, a series of five targets 1-5 correspond to sample tubes held in a sample tube rack such as the rack 44 of FIG. 1. Repeated bursts of ultrasonic energy such as the burst 150 are emitted by the transducer 12 at fixed time intervals while the targets 1, 2, 3, 4 and 5 move at a fixed velocity underneath the transducer 12 in a scan direction 156.

Figure 7:
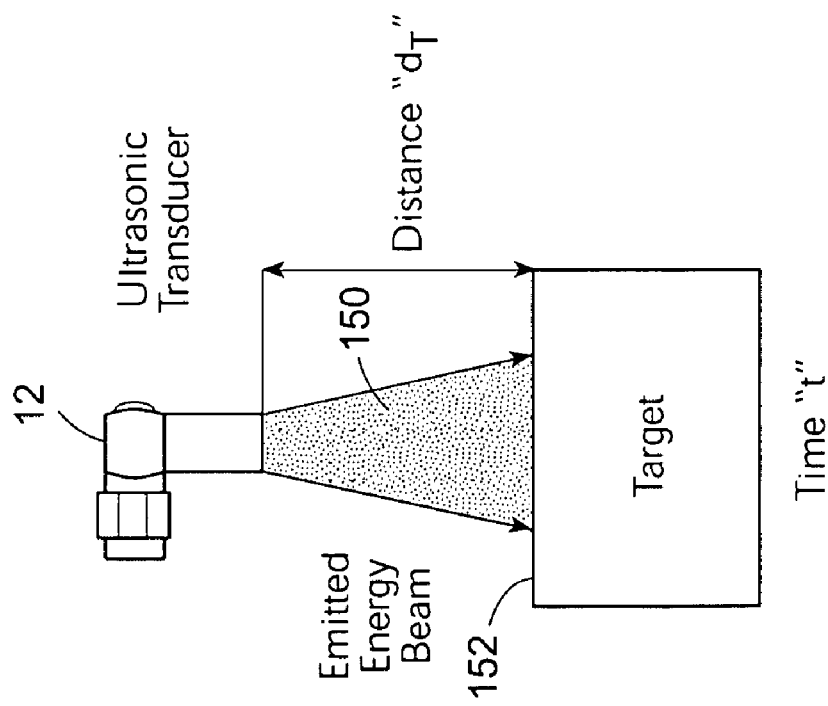
Figure 9:
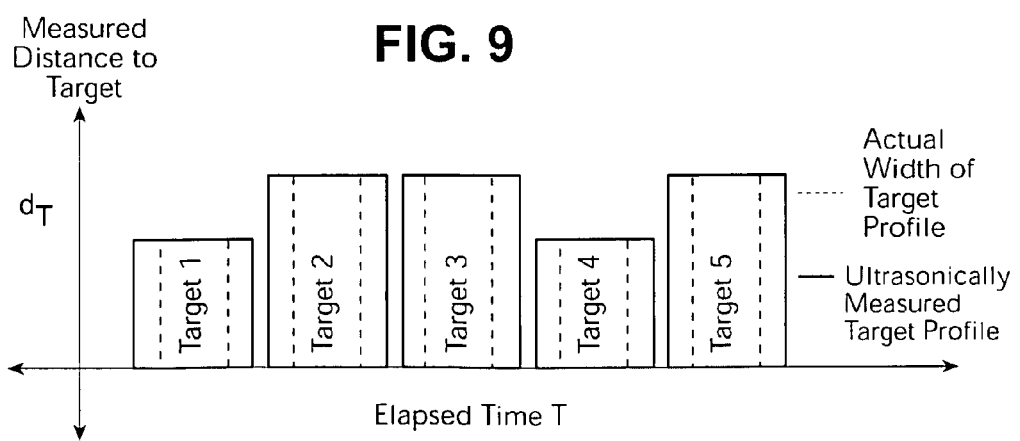
FIG. 9 is a simplified schematic view of the target profile provided by the ultrasonic liquid level sensing system of FIG. 8.

Referring to FIG. 9, a measured distance to target ($d_T$) from the transducer 12 for each echo from a reflected beam such as the beam 154 of FIG. 7 versus elapsed (T) time is plotted in increments corresponding to selected fixed time intervals during which repeated bursts of ultrasonic energy are emitted. The actual width of the target profile is shown in dotted outline in FIG. 9 whereas the ultrasonically measured target profile is shown in solid outline in FIG. 9. A continuous outline of the targets 1, 2, 3, 4 and 5 is thus generated. Because of the diverging conical shape of the ultrasonic burst 150 and the diverging width of the reflected beam 154 such as shown in FIG. 7 the ultrasonically measured target profile can appear to be much wider than the actual width of the target structure.

Figure 10:
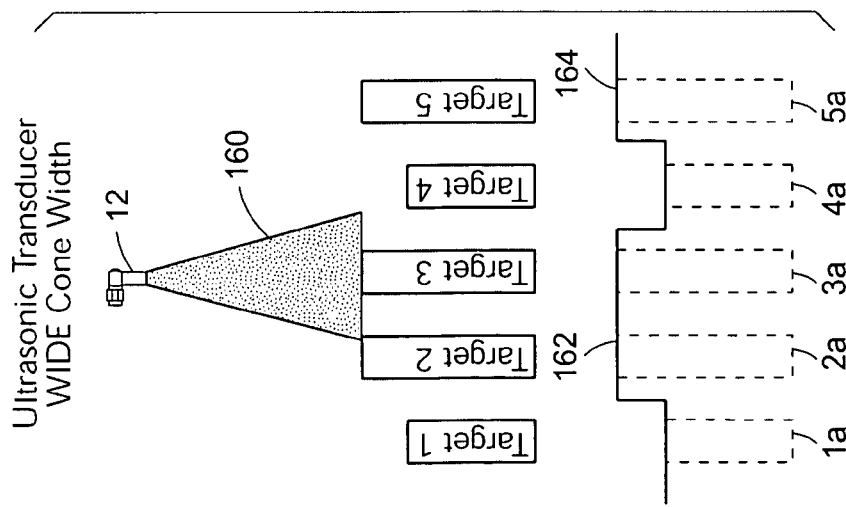

Referring to FIG. 10, an ultrasonic transducer 12 is arranged to emit an ultrasonic burst 160 having a relatively wide cone-width that overshadows more than one of the targets 1, 2, 3, 4 and 5 during a profiling operation. It will be noted that the dotted outlines 1a, 2a, 3a, 4a and 5a shown at the lower portion of FIG. 10 correspond to the actual target profile of the targets 1-5, whereas the solid outlines such as 162 and 164 correspond to the measured profile of the targets 1-5. However, because of the relatively wide cone-width of the ultrasonic burst 160 and the corresponding wide range of the reflected energy beam of the type shown as reference number 154 in FIG. 7, there is a low resolution ultrasonic profiling of the targets 1, 2, 3, 4 and 5 which makes it difficult to ultrasonically distinguish between the individual targets 1, 2, 3, 4 and 5.

Figure 11:
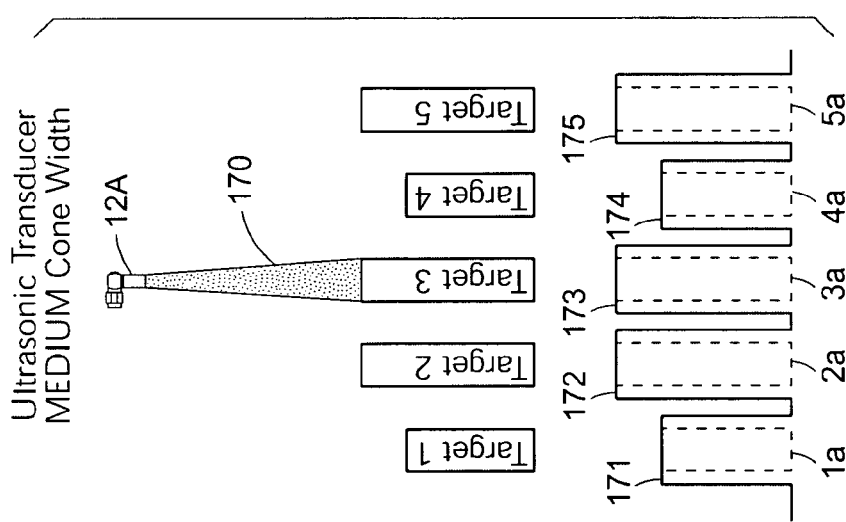

Referring to FIG. 11, an ultrasonic transducer 12A is arranged to emit an ultrasonic burst 170 having a relatively medium cone-width in comparison with the ultrasonic burst 160 of FIG. 10. The ultrasonic burst 170 produces a beam echo profile of the targets 1-5 wherein the ultrasonically measured target profile, shown in solid outlines 171, 172, 173, 174 and 175, extend slightly beyond the actual width of the target profiles shown in dotted outline at 1a, 2a, 3a, 4a and 5a.

Figure 12:
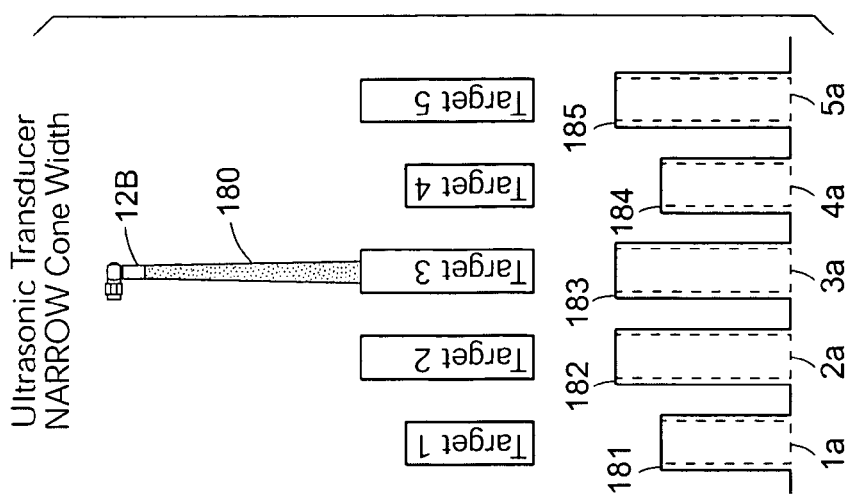
FIGS. 10, 11 and 12 are simplified schematic views of ultrasonic liquid level sensing systems with transducer beams of different cone-width and the corresponding target profiles produced by the beams of different cone-width.

Referring to FIG. 12, an ultrasonic transducer 12B is arranged to emit an ultrasonic burst 180 having a relatively narrow cone-width in comparison with the ultrasonic burst 170 of FIG. 11. The ultrasonic burst 180 produces a beam-echo profile of the targets 1-5 below. The ultrasonically measured target profile, shown in solid outlines 181, 182, 183, 184 and 185 closely conforms to the actual target profiles, shown in dotted outline at 1a, 2a, 3a, 4a and 5a. Thus the narrow cone-width ultrasonic burst 180 yields higher resolution of the physical size of the targets 1-5.

Since a transducer beam of relatively narrow cone-width such as the beam 180 yields higher resolution than a transducer beam of relatively wide cone-width such as the beam 160, it is usually preferable to select a transducer having an ultrasonic crystal that is capable of producing a transducer beam of relatively narrow cone-width.

Generally ultrasonic crystals produce emitted energy at a level that corresponds to the size of the crystal. Relatively small ultrasonic crystals produce relatively lower emitted energy than a relatively large ultrasonic crystal, and have a relatively lower sensing range. However, a relatively low sensing range can make it difficult to obtain high resolution ultrasonic profiles of distant targets.

Oftentimes in order to reach a desired sensing range, it is necessary to utilize a transducer having a crystal that emits a relatively high level of energy. However, a relatively high level of emitted energy usually comes from a transducer that emits an ultrasonic burst of relatively wide cone-width. Compromises must thus be made between the need for high resolution versus high sensing ranges.

Figure 13A:
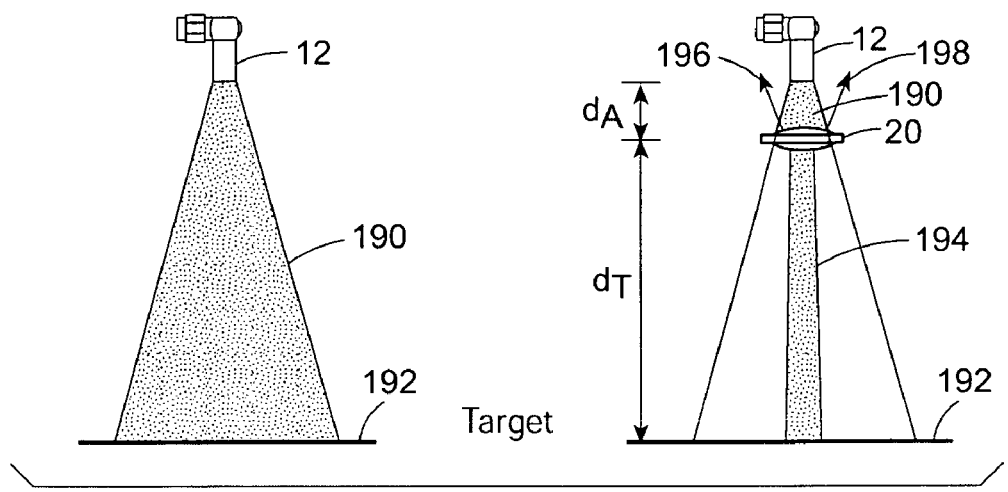
FIG. 13A is a simplified schematic view of an ultrasonic liquid level sensing system that emits a transducer beam with a wide cone-width.
Figure 13B:
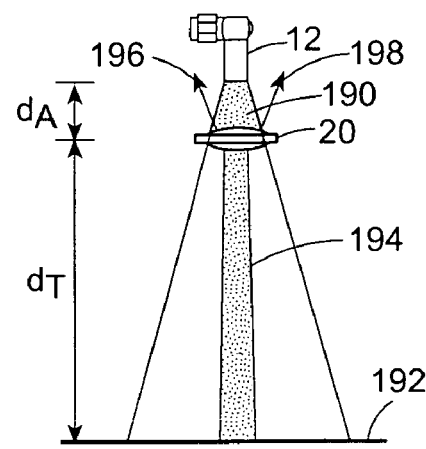
FIG. 13B is a view similar to FIG. 13A wherein the emitted transducer beam of wide cone-width is reshaped by the beam shaping device of the present invention to form an emitted transducer beam of narrow cone-width.

Referring to FIG. 13A, the ultrasonic transducer module 12 produces an emitted energy burst 190 of relatively wide cone-width that strikes the target 192. Referring to FIG. 13B, the beam shaping element 20 is positioned a predetermined distance $d_A$ below the transducer module 12 and a predetermined distance $d_T$ from the target 192. The beam shaping element 20 reshapes the emitted energy of the relatively wide transducer beam 190 such that only a central portion 194 of the transducer beam 190 is permitted to pass through the central cylindrical aperture 120 (FIG. 4) of the beam shaping element 20.

Portions of the emitted transducer beam 190 that are radially beyond the central aperture 120 (FIG. 4) of the beam shaping element 20 are blocked by the beam shaping element 20 and are reflected off the upper conical surface 112 (FIG. 4) of the beam shaping element 20. The blocked, reflected rays, also referred to as extraneous, unusable portions of the transducer beam, are schematically indicated at reference numbers 196 and 198 in FIG. 13B. The blocked and reflected portions 196 and 198 of the transducer beam 190 are thus diverted away from the transducer module 12 based on the selected conical angle of the conical surface 112. The central beam portion 194 has the same high level of emitted energy as the relatively wide transducer beam 190. The central beam portion 194 also provides the high resolution qualities that are normally associated with a relatively narrow cone-width transducer beam of relatively low emitted energy.

Figure 14A:
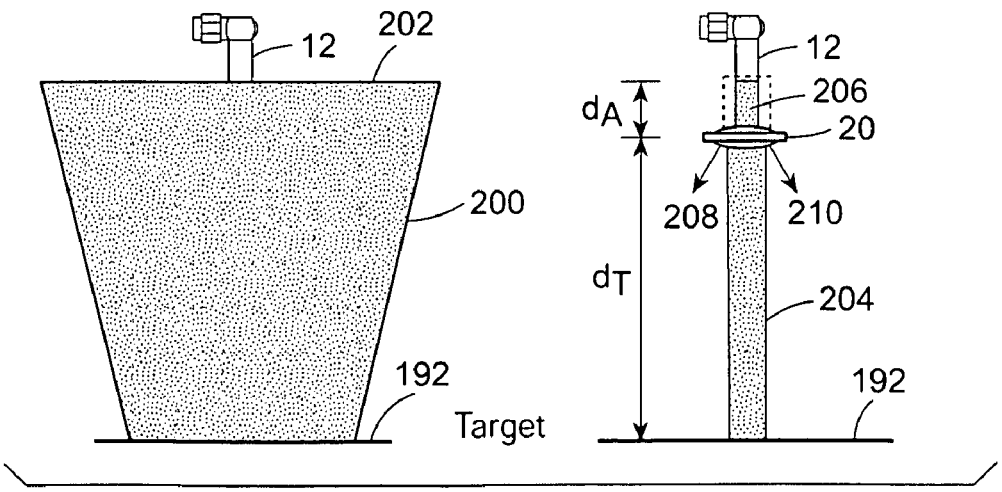
FIG. 14A is a view similar to FIG. 13A showing the transducer beam of wide cone-width reflected from a target; and, FIG. 14B is a view similar to FIG. 13B showing the reshaped beam reflected from a target back toward the beam shaping device of the present invention and toward the transducer.

Referring to FIG. 14A, a reflected beam 200, produced by the ultrasonic burst 190 of FIG. 13A is reflected from the target 192. The reflected beam 200 has a relatively wide cone-width as indicated at reference number 202 (FIG. 14A). The cone-width 202 can range well beyond the physical extremity of the target 192 resulting in a low resolution of the target 192, as schematically indicated in the ultrasonic images 162 and 164 of FIG. 10.

Figure 14B:
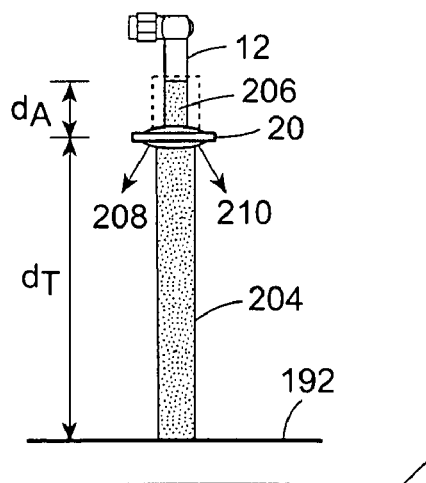

Referring to FIGS. 13B and 14B, the transmitted central beam portion 194 of FIG. 13B is reflected from the target 192 as a reflected beam 204 (FIG. 14B) directed upwardly from the target 192 toward the transducer 12. The beam shaping element 20 also reshapes the reflected beam 204 such that only a beam portion 206 of the reflected beam 204 passes through the central aperture 120 (FIG. 4) of the beam shaping element 20. Therefore only the central beam portion 206 returns to the transducer 12.

Portions of the reflected beam 204 that are radially beyond the central aperture 120 (FIG. 4) of the beam shaping element 20 are blocked by the lower conical surface 114 (FIG. 4) of the beam shaping element 20 and are reflected off the lower conical surface 114 as schematically indicated at reference numbers 208 and 210 in FIG. 14B.

In this manner, the unusable and extraneous portions 208 and 210 are diverted away from the transducer module 12 based on the selected conical angle of the conical surface 114.

The central beam portion 206 that is reflected back to the transducer 12 has approximately the same high level of emitted energy as the relatively wide cone-width transducer beam 190 of FIGS. 13A and 13B. The high energy central beam portion 206 also provides the high resolution qualities that are normally associated with a relatively low emitted energy beam of relatively narrow cone-width such as the beam 180 of FIG. 12.

In summary, the beam shaping element 20 reshapes the transmitted high energy beam 190 (FIG. 13B). The beam shaping element 20 forms a high energy central beam portion 194 of relatively narrow width from the high energy beam 190. The high energy central beam 194 that is reflected from the target 192 as the high energy reflected beam 204 is also reshaped by the beam shaping element 20 to form the high energy central beam portion 206. Only the central beam portion 206 returns to the transducer 12.

Thus unusable and extraneous outer sections of reflections and echoes such as the rays 196 and 198 (FIG. 13B) and the rays 208 and 210 (FIG. 14B) that cannot pass through the central aperture 120 of the beam shaping element 20 are diverted from the receiving portion of the transducer 12. The beam shaping element 20 thereby enables the liquid level sensing system to use a high energy transducer beam to provide a high resolution, high sensing range, and distinctive profiling of sample tubes that pass beneath the transducer 12, such as the targets 1-5 of FIGS. 8-12.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. An ultrasonic beam shaping device comprising,
a) a plate-like beam shaping element formed of opaque material, said beam shaping element having first and second conical surfaces formed as opposite surface portions of said beam shaping element, said first and second conical surfaces having respective first and second axes, said first and second axes being co-axial,
b) a cylindrical aperture in said beam shaping element formed along the co-axial axes of said first and second conical surfaces, said cylindrical aperture having a central axis co-axial with the first and second co-axial axes of said conical surfaces, said cylindrical aperture intersecting said first and second conical surfaces to form a first circular open end of said aperture at said first conical surface and a second circular open end of said cylindrical aperture at said second conical surface,
c) a mounting plate for an ultrasonic transmitter and means for adjusting the distance between said beam shaping element and the mounting plate,
d) and wherein said means for adjusting the distance between said beam shaping element and said mounting plate include spacer legs joining said beam shaping element and said mounting plate to permit adjustable movement of said beam shaping element relative to said mounting plate.

2. An ultrasonic beam shaping device comprising,
a) a plate-like beam shaping element formed of opaque material, said beam shaping element having first and second conical surfaces formed as opposite surface portions of said beam shaping element, said first and second conical surfaces having respective first and second axes, said first and second axes being co-axial,
b) a cylindrical aperture in said beam shaping element formed along the co-axial axes of said first and second conical surfaces, said cylindrical aperture having a central axis co-axial with the first and second co-axial axes of said conical surfaces, said cylindrical aperture intersecting said first and second conical surfaces to form a first circular open end of said aperture at said first conical surface and a second circular open end of said cylindrical aperture at said second conical surface,
c) a mounting plate for an ultrasonic transmitter and means for adjusting the distance between said beam shaping element and the mounting plate,
d) and wherein said beam shaping element includes an annular peripheral rim extending radially beyond the first and second conical surfaces relative to the central axis of said cylindrical aperture and said means for adjusting the distance between said beam shaping element and said mounting plate include spacer legs on said annular peripheral rim joining said beam shaping element and said mounting plate to permit adjustable movement of said beam shaping element relative to said mounting plate.

3. An ultrasonic beam shaping device comprising,
a) a plate-like beam shaping element formed of opaque material, said beam shaping element having first and second conical surfaces formed as opposite surface portions of said beam shaping element, said first and second conical surfaces having respective first and second axes, said first and second axes being co-axial,
b) a cylindrical aperture in said beam shaping element formed along the co-axial axes of said first and second conical surfaces, said cylindrical aperture having a central axis co-axial with the first and second co-axial axes of said conical surfaces, said cylindrical aperture intersecting said first and second conical surfaces to form a first circular open end of said aperture at said first conical surface and a second circular open end of said cylindrical aperture at said second conical surface
c) and wherein said beam shaping element includes an annular peripheral rim extending radially beyond the first and second conical surfaces relative to the central axis of said cylindrical aperture.

4. An ultrasonic beam shaping device comprising,
a) a plate-like beam shaping element formed of opaque material, said beam shaping element having first and second conical surfaces formed as opposite surfaces of said beam shaping element, said first and second conical surfaces each having an axis, and each said axis being co-axial, a cylindrical aperture formed in said beam shaping element along the co-axial axes of said first and second conical surfaces and extending through said first and second conical surfaces such that said cylindrical aperture has a central axis that is co-axial with the axes of said first and second conical surfaces,
b) a mounting plate for an ultrasonic transducer, said mounting plate including a beam emission opening of greater diametrical magnitude than the diameter of said cylindrical aperture,
c) spacer means connected to said mounting plate and said beam shaping element to maintain a predetermined distance between said mounting plate and the cylindrical aperture in said beam shaping element, and to maintain alignment between said beam emission opening and said cylindrical aperture, such that a beam emitted by an ultrasonic transducer can pass through the beam emission opening, and a predetermined portion of the beam that passes through the beam emission opening passes through the cylindrical aperture of said beam shaping element,
d) means for adjusting the distance between said beam shaping element and the mounting plate,
e) and wherein said means for adjusting the distance between said beam shaping element and said mounting plate include spacer legs joining said beam shaping element and said mounting plate to permit adjustable movement of said beam shaping element relative to said mounting plate.

5. The ultrasonic beam shaping device as claimed in claim 4 wherein said beam shaping element includes an annular peripheral rim extending radially beyond the first and second conical surfaces relative to the central axis of said cylindrical aperture and said means for adjusting the distance between said beam shaping element and said mounting plate include spacer legs on said annular peripheral rim joining said beam shaping element and said mounting plate to permit adjustable movement of said beam shaping element relative to said mounting plate.

6. An ultrasonic beam shaping device comprising,
a) a plate-like beam shaping element formed of opaque material, said beam shaping element having first and second conical surfaces formed as opposite surfaces of said beam shaping element, said first and second conical surfaces each having an axis, and each said axis being co-axial, a cylindrical aperture formed in said beam shaping element along the co-axial axes of said first and second conical surfaces and extending through said first and second conical surfaces such that said cylindrical aperture has a central axis that is co-axial with the axes of said first and second conical surfaces,
b) a mounting plate for an ultrasonic transducer, said mounting plate including a beam emission opening of greater diametrical magnitude than the diameter of said cylindrical aperture,
c) spacer means connected to said mounting plate and said beam shaping element to maintain a predetermined distance between said mounting plate and the cylindrical aperture in said beam shaping element, and to maintain alignment between said beam emission opening and said cylindrical aperture, such that a beam emitted by an ultrasonic transducer can pass through the beam emission opening, and a predetermined portion of the beam that passes through the beam emission opening passes through the cylindrical aperture of said beam shaping element, and
d) wherein said beam shaping element includes an annular peripheral rim extending radially beyond the first and second conical surfaces relative to the central axis of said cylindrical aperture.

7. The ultrasonic beam shaping device as claimed in claim 6 further including a mounting member with a receiving bore for receiving an ultrasonic transducer to hold the ultrasonic transducer in a fixed position within the mounting member, and including joining means for joining the mounting plate to the mounting member.

8. An ultrasonic beam shaping device comprising,
a) a plate-like beam shaping element formed of opaque material, said beam shaping element having first and second opposite surface portions in the form of respective first and second conical surfaces having respective first and second axes, said first conical surface converging toward said first axis in a direction away from said second conical surface and said second conical surface converging toward said second axis in a direction away from said first conical surface, and said first and second conical surfaces extending 360° around their respective first and second axes,
b) an aperture extending through said beam shaping element to form a first open end at said first conical surface and a second open end at said second conical surface,
c) said beam shaping element including mounting means for mounting said beam shaping element in alignment with an ultrasonic transducer that emits ultrasonic beams,
  (i) to permit one portion of an ultrasonic beam emitted by the ultrasonic transducer to pass in a first direction away from the transducer through said aperture, and, upon reflection of said ultrasonic transducer beam back toward said ultrasonic transducer
  (ii) to permit one portion of the reflected beam to pass in a second direction, opposite the first direction through said aperture back to said ultrasonic transducer,
d) the first cone angle of said first conical surface being selected to permit portions of an ultrasonic beam that reflect off said first conical surface to reflect radially away from the periphery of the first open end of the aperture, and the second cone angle of said second conical surface being selected to permit portions of an ultrasonic beam that reflect off said second conical surface to reflect away from the periphery of the second open end of said aperture,
e) a mounting plate for an ultrasonic transducer and means for adjusting the distance between said beam shaping element and the mounting plate, and
f) wherein said means for adjusting the distance between said beam shaping element and said mounting plate include spacer legs joining said beam shaping element and said mounting plate to permit adjustable movement of said beam shaping element relative to said mounting plate.

9. An ultrasonic beam shaping device comprising,
a) a plate-like beam shaping element formed of opaque material, said beam shaping element having first and second opposite surface portions in the form of respective first and second conical surfaces having respective first and second axes, said first conical surface converging toward said first axis in a direction away from said second conical surface and said second conical surface converging toward said second axis in a direction away from said first conical surface, and said first and second conical surfaces extending 360° around their respective first and second axes, b) an aperture extending through said beam shaping element to form a first open end at said first conical surface and a second open end at said second conical surface, c) said beam shaping element including mounting means for mounting said beam shaping element in alignment with an ultrasonic transducer that emits ultrasonic beams,
   (i) to permit one portion of an ultrasonic beam emitted by the ultrasonic transducer to pass in a first direction away from the transducer through said aperture, and, upon reflection of said ultrasonic transducer beam back toward said ultrasonic transducer,
   (ii) to permit one portion of the reflected beam to pass in a second direction, opposite the first direction through said aperture back to said ultrasonic transducer, d) the first cone angle of said first conical surface being selected to permit portions of an ultrasonic beam that reflect off said first conical surface to reflect radially away from the periphery of the first open end of the aperture, and the second cone angle of said second conical surface being selected to permit portions of an ultrasonic beam that reflect off said second conical surface to reflect away from the periphery of the second open end of said aperture, e) a mounting plate for an ultrasonic transducer and means for adjusting the distance between said beam shaping element and the mounting plate, and f) wherein said beam shaping element includes an annular peripheral rim extending radially beyond the first and second conical surfaces relative to the central axis of said cylindrical aperture and said means for adjusting the distance between said beam shaping element and said mounting plate include spacer legs on said annular peripheral rim joining said beam shaping element and said mounting plate to permit adjustable movement of said beam shaping element relative to said mounting plate.

10. An ultrasonic beam shaping device comprising, a) a plate-like beam shaping element formed of opaque material, said beam shaping element having first and second opposite surface portions in the form of respective first and second conical surfaces having respective first and second axes, said first conical surface converging toward said first axis in a direction away from said second conical surface and said second conical surface converging toward said second axis in a direction away from said first conical surface, and said first and second conical surfaces extending 360° around their respective first and second axes, b) an aperture extending through said beam shaping element to form a first open end at said first conical surface and a second open end at said second conical surface, c) said beam shaping element including mounting means for mounting said beam shaping element in alignment with an ultrasonic transducer that emits ultrasonic beams,
   (i) to permit one portion of an ultrasonic beam emitted by the ultrasonic transducer to pass in a first direction away from the transducer through said aperture, and, upon reflection of said ultrasonic transducer beam back toward said ultrasonic transducer,
   (ii) to permit one portion of the reflected beam to pass in a second direction, opposite the first direction through said aperture back to said ultrasonic transducer, d) the first cone angle of said first conical surface being selected to permit portions of an ultrasonic beam that reflect off said first conical surface to reflect radially away from the periphery of the first open end of the aperture, and the second cone angle of said second conical surface being selected to permit portions of an ultrasonic beam that reflect off said second conical surface to reflect away from the periphery of the second open end of said aperture, and e) wherein said aperture is a cylindrical aperture having a central axis and said beam shaping element includes an annular peripheral rim extending radially beyond the first and second conical surfaces relative to the central axis of said cylindrical aperture.

11. A beam shaping device as claimed in claim 10 further including a mounting member with a receiving bore for receiving an ultrasonic transducer to hold the ultrasonic transducer in a fixed position within the mounting member, and including joining means for joining the mounting plate to the mounting member.

12. A method of reducing ultrasonic reflections and echoes from a target during ultrasonic liquid level sensing comprising, a) providing a support base with a beam emission opening for an ultrasonic transducer and supporting the ultrasonic transducer on one side of the support base in alignment with the beam emission opening such that a beam emitted from the ultrasonic transducer passes through the beam emission opening in the support base, b) making the beam emission opening in the support base large enough to permit substantially the entire transducer beam to pass through the beam emission opening, c) supporting an opaque beam shaping element away from the other side of the support base, d) making a cylindrical aperture in the beam shaping element smaller than the beam emission opening in the support base and aligning the cylindrical aperture with the beam emission opening such that the difference in size between the beam emission opening and the cylindrical aperture permits only a portion of the ultrasonic beam from the ultrasonic transducer to be directed through the cylindrical aperture of the beam shaping element toward a target, e) forming the beam shaping element with two conical surfaces oriented base-to-base such that the cylindrical aperture passes through the conical surfaces, and the axis of the cylindrical aperture and the axis of each of the conical surfaces are co-axial, whereby the portion of the ultrasonic beam that is beyond the border of the cylindrical aperture and does not pass through the cylindrical aperture from the ultrasonic transducer is directed against one of the conical surfaces for reflection in directions away from the ultrasonic transducer and away from an intended target, and whereby any portion of the ultrasonic beam reflected from an intended target that is beyond the border of the cylindrical aperture and does not pass through the cylindrical aperture from the intended target but is directed against the other of the conical surfaces is reflected from the other of the conical surfaces in directions away from the ultrasonic transducer and away from the intended target, f) wherein the step of supporting the beam shaping element includes forming an annular peripheral rim to extend radially beyond the first and second conical surfaces relative to the axis of each of the conical surfaces, and g) adjusting the distance between the peripheral rim of the beam shaping element and the support base to a first selectable distance to obtain a first predetermined intensity of ultrasonic beam passing through the cylindrical aperture from the ultrasonic transducer.

13. The method as claimed in claim 12 including adjusting the distance between the beam shaping element and the intended target to a second selectable distance to obtain a second predetermined intensity of the reflected ultrasonic beam passing through the cylindrical aperture from the intended target.

* * * * *